(12) United States Patent
Harrison

(10) Patent No.: US 6,605,110 B2
(45) Date of Patent: Aug. 12, 2003

(54) STENT WITH ENHANCED BENDABILITY AND FLEXIBILITY

(75) Inventor: William J. Harrison, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/896,947

(22) Filed: Jun. 29, 2001

(65) Prior Publication Data

US 2003/0014101 A1 Jan. 16, 2003

(51) Int. Cl.[7] .................................................. A61F 2/06
(52) U.S. Cl. ..................................................... 623/1.15
(58) Field of Search .................................. 623/1.15–1.2

(56) References Cited

U.S. PATENT DOCUMENTS

| | | |
|---|---|---|
| 4,241,146 A | 12/1980 | Sivachenko et al. |
| 4,725,334 A | 2/1988 | Brimm |
| 4,728,328 A | 3/1988 | Hughes et al. |
| 4,733,665 A | 3/1988 | Palmaz |
| 4,739,762 A | 4/1988 | Palmaz |
| 4,762,128 A | 8/1988 | Rosenbluth |
| 4,776,337 A | 10/1988 | Palmaz |
| 4,830,003 A | 5/1989 | Wolff et al. |
| 4,893,623 A | 1/1990 | Rosenbluth |
| 4,986,831 A | 1/1991 | King et al. |
| 5,019,090 A | 5/1991 | Pinchuk |
| 5,064,435 A | 11/1991 | Porter |
| 5,102,417 A | 4/1992 | Palmaz |
| 5,104,404 A | 4/1992 | Wolff |
| 5,108,417 A | 4/1992 | Sawyer |
| 5,133,732 A | 7/1992 | Wiktor |
| 5,135,536 A | 8/1992 | Hillstead |
| 5,195,984 A | 3/1993 | Schatz |
| 5,282,823 A | 2/1994 | Schwartz et al. |
| 5,344,425 A | 9/1994 | Sawyer |
| 5,354,308 A | 10/1994 | Simon et al. |
| 5,366,504 A | 11/1994 | Andersen et al. |
| 5,383,892 A | 1/1995 | Cardon et al. |
| 5,395,390 A | 3/1995 | Simon et al. |

(List continued on next page.)

FOREIGN PATENT DOCUMENTS

| | | |
|---|---|---|
| DE | 195 37 872 A | 4/1997 |
| DE | 197 46 882 A1 | 4/1999 |

(List continued on next page.)

OTHER PUBLICATIONS

U.S. patent application Ser. No. 0039447, Pinchasik et al., filed Nov. 8, 2001.

(List continued on next page.)

Primary Examiner—David H. Willse
Assistant Examiner—Suzette J. Jackson
(74) Attorney, Agent, or Firm—Fulwider Patton Lee & Utecht, LLP

(57) ABSTRACT

The invention is directed to an expandable self-expanding stent for implantation in a body lumen, such as an artery. The stent is made with a plurality of cylindrical elements which are interconnected by a plurality of interconnecting members which connect adjacent cylindrical elements, some of the interconnecting members have one or more bending points formed therein for promoting the bendability of the interconnecting member. The bending point can be formed by reducing the strut wall thickness of the interconnecting member to promote the bending of the strut or it can be formed by reducing the strut width of the interconnecting member, or a combination of both. The bending points on the interconnecting member enhances the bendability and flexibility of the composite stent device by creating mechanical hinges which help to bend the stent as it is delivered through the tortuous anatomy of the patient or conforms to a curved portion of a body vessel, where the stent may be implanted.

19 Claims, 4 Drawing Sheets

U.S. PATENT DOCUMENTS

| | | |
|---|---|---|
| 5,413,597 A | 5/1995 | Krajicek |
| 5,421,955 A | 6/1995 | Lau et al. |
| 5,449,373 A | 9/1995 | Pinchasik et al. |
| 5,476,506 A | 12/1995 | Lunn |
| 5,514,154 A | 5/1996 | Lau et al. |
| 5,527,324 A | 6/1996 | Krantz et al. |
| 5,569,295 A | 10/1996 | Lam |
| 5,601,593 A | 2/1997 | Freitag |
| 5,630,829 A | 5/1997 | Lauterjung |
| 5,636,641 A | 6/1997 | Fariabi |
| 5,681,346 A | 10/1997 | Orth et al. |
| 5,693,089 A | 12/1997 | Inoue |
| 5,707,388 A | 1/1998 | Lauterjung |
| 5,716,393 A | 2/1998 | Lindenberg et al. |
| 5,741,327 A | 4/1998 | Frantzen |
| 5,759,192 A | 6/1998 | Saunders |
| 5,776,161 A | 7/1998 | Globerman |
| 5,807,404 A | 9/1998 | Richter |
| 5,810,868 A | 9/1998 | Lashinski et al. |
| 5,836,966 A | 11/1998 | St. Germain |
| 5,843,120 A | 12/1998 | Israel et al. |
| 5,843,175 A | 12/1998 | Frantzen |
| 5,868,783 A | 2/1999 | Tower |
| 5,913,895 A | 6/1999 | Burpee et al. |
| 5,922,021 A | 7/1999 | Jang |
| 6,019,789 A | 2/2000 | Dinh et al. |
| 6,027,526 A | 2/2000 | Limon et al. |
| 6,042,597 A | 3/2000 | Kveen et al. |
| 6,042,606 A | 3/2000 | Frantzen |
| 6,099,561 A | 8/2000 | Alt |
| 6,183,506 B1 | 2/2001 | Penn et al. |
| 6,187,034 B1 * | 2/2001 | Frantzen ................ 623/11.11 |
| 6,203,569 B1 * | 3/2001 | Wijay ..................... 623/1.15 |
| 6,214,042 B1 * | 4/2001 | Jacobsen et al. ............ 623/1.2 |
| 6,217,608 B1 | 4/2001 | Penn et al. |
| 6,231,598 B1 | 5/2001 | Berry et al. |
| 6,245,101 B1 | 6/2001 | Drasler et al. |
| 6,344,055 B1 * | 2/2002 | Shukov .................. 623/1.15 |
| 6,375,677 B1 * | 4/2002 | Penn et al. ............... 623/1.16 |
| 6,409,753 B1 * | 6/2002 | Brown et al. ............. 623/1.15 |
| 6,416,543 B1 * | 7/2002 | Hilaire et al. ............. 623/1.16 |

FOREIGN PATENT DOCUMENTS

| | | |
|---|---|---|
| EP | 0 201 466 A | 11/1986 |
| EP | 0 540 290 A | 5/1993 |
| EP | 0 541 443 A | 5/1993 |
| EP | 0 606 165 | 7/1994 |
| EP | 0 669 114 A1 | 8/1995 |
| EP | 0 669 114 B1 | 8/1995 |
| EP | 0 688 545 A | 12/1995 |
| EP | 0 800 801 | 10/1997 |
| EP | 0 806 190 | 11/1997 |
| EP | 0 928 605 A2 | 7/1999 |
| EP | 1 042 997 A1 | 10/2000 |
| EP | 0 888 093 B1 | 7/2001 |
| FR | 2 764 794 | 12/1998 |
| WO | WO 94/17754 | 8/1994 |
| WO | WO 95/23563 | 9/1995 |
| WO | WO 05/26695 | 10/1995 |
| WO | WO 95/33422 | 12/1995 |
| WO | WO 96/03092 A1 | 2/1996 |
| WO | WO 96/09013 | 3/1996 |
| WO | WO 97/32543 | 9/1997 |
| WO | WO 98/22159 | 5/1998 |
| WO | WO 98/58600 | 12/1998 |
| WO | WO 99/15108 | 4/1999 |

OTHER PUBLICATIONS

U.S. patent application Ser. No. 0041929, Oepen, filed Nov. 15, 2001.

U.S. patent application Ser. No. 0041930, Globerman et al., filed Nov. 15, 2001.

U.S. patent application Ser. No. 09/343,962 filed Jun. 30, 1999.

* cited by examiner

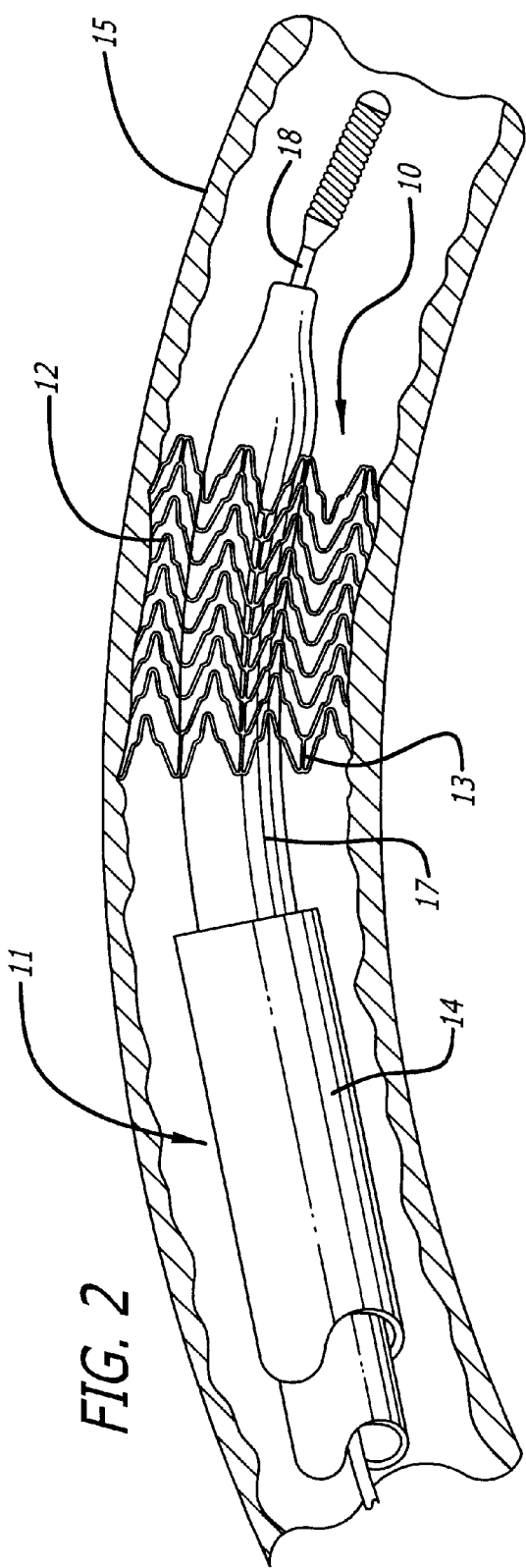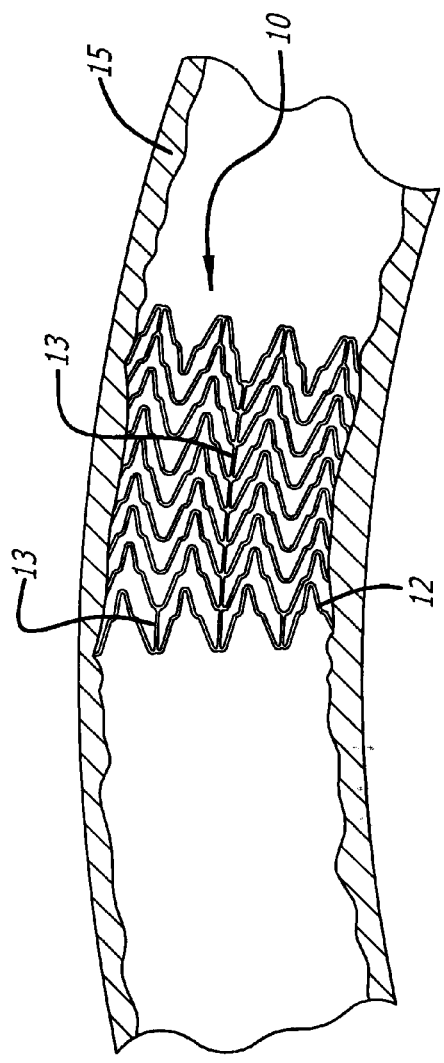
FIG. 2
FIG. 3

STENT WITH ENHANCED BENDABILITY AND FLEXIBILITY

BACKGROUND OF THE INVENTION

This invention relates to expandable endoprosthesis devices, generally called stents, which are adapted to be implanted into a patient's body lumen, such as a blood vessel, to maintain the patency thereof. These devices are particularly useful in the treatment and repair of blood vessels after a stenosis has been compressed by percutaneous transluminal coronary angioplasty (PTCA), percutaneous transluminal angioplasty (PTA), or removed by atherectomy, laser angioplasty or other means.

Several interventional treatment modalities are presently used for heart disease, including balloon and laser angioplasty, atherectomy, and by-pass surgery. In typical coronary balloon angioplasty procedures, a guiding catheter having a distal tip is percutaneously introduced through the femoral artery into the cardiovascular system of a patient using a conventional Seldinger technique and advanced within the cardiovascular system until the distal tip of the guiding catheter is seated in the ostium of a coronary artery. A guide wire is positioned within an inner lumen of a dilatation catheter and then both are advanced through the guiding catheter to the distal end thereof. The guide wire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guide wire until the balloon of the dilatation catheter is properly positioned across the lesion. Once in position across the lesion, the balloon is inflated to compress the plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guide wires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,507,768 (Lau, et al.); U.S. Pat. No. 5,451,233 (Yock); and U.S. Pat. No. 5,458,651 (Klemm, et al.).

One problem that can occur during balloon angioplasty procedures is the formation of intimal flaps which can collapse and occlude the artery when the balloon is deflated at the end of the angioplasty procedure. Another problem characteristic of balloon angioplasty procedures is the large number of patients who are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A focus of recent development work in the treatment of heart disease has been directed to endoprosthetic devices called stents. Stents are generally cylindrically shaped intravascular devices which are placed within an artery to hold it open. The device can be used to reduce the likelihood of restenosis and to maintain the patency of a blood vessel immediately after intravascular treatments. In some circumstances, they can also be used as the primary treatment device where they are expanded to dilate a stenosis and then left in place. Further details of stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); U.S. Pat. No. 4,886,062 (Wiktor); U.S. Pat. No. 5,421,955 (Lau); and U.S. Pat. No. 5,569,295 (Lam).

A variety of stent designs have been developed and include coiled wires in a variety of patterns that are expanded after being placed intraluminally on a balloon catheter; helically wound coiled springs manufactured from expandable heat sensitive metals; self-expanding stents inserted in a compressed state for deployment in a body lumen, and stents shaped in zig zag patterns. One of the difficulties encountered using prior art stents involve maintaining the radial rigidity needed to hold open a body lumen while at the same time maintaining the longitudinal flexibility of the stent to facilitate its delivery and accommodate the often tortuous path of the patient's vasculature. Generally, the greater the longitudinal flexibility of the stent, the easier and more safely it can be delivered to the implantation site.

Various means have been described to deliver and implant stents. One method frequently described for delivering of a stent to a desired intraluminal location includes mounting the stent on an expandable member, such as a balloon on a distal end of an intravascular catheter, advancing the catheter to the desired location within the patient's vascular system, inflating the balloon on the catheter to expand the stent into a permanent expanded condition. The expandable member is then deflated and the catheter is withdrawn, leaving the expanded stent within the blood vessel, holding open the passageway thereof. Other prior art stent delivery catheters used for implanting self-expanding stents include an inner member upon which the compressed or collapsed stent is mounted and an outer restraining sheath which is placed over the compressed stent to maintain it in its compressed state prior to deployment. When the stent is to be deployed in the body vessel, the outer restraining sheath is retracted in relation to the inner lumen to uncover the compressed stent, allowing the stent to move into its expanded condition for implantation in the patient.

Advancing the stent through a patient's vasculature, which can involve traversing sharp bends and other obstacles, may require the stent to be highly flexible. While it is beneficial if the area of treatment is located in a substantially straight portion of the patient's vasculature, often, the area of treatment is at a curved portion of the body vessel which can be problematic to the physician when implanting the device. Therefore, stent flexibility must permit the stent to be deployed in and conform to a tortuous section of a patient's vasculature. Moreover, once implanted, the stent should not attempt to straighten the curved vessel since this could possibly cause disruption in the normal flow of the blood through the vessel and could possibly result in restenosis occurring at that location. Additionally, visualization of the stent with a fluoroscope, which is currently the most widely used method of locating and positioning the stent during deployment, requires a stent with good radiopacity.

Different methods have been attempted to give stents high flexibility and radiopacity. By making stents out of relatively thin material, flexibility can be increased. However, the use of thin material can reduce the radiopacity of the stent, making it more difficult for the physician to visualize the stent. Conversely, the use of thicker material, which can promote radiopacity results in reduced stent flexibility, which can impair the deliverability of the stent. When the stent is made from a self-expanding material, such as nickel titanium, which has less radiopacity than a stainless steel stent, for example, the problem of visualizing the self-expanding stent can be further increased if thinner material is used to increase flexibility.

An early attempt at achieving a flexible stent with good radiopacity characteristics involved providing a stent of a base material with good flexibility and strength but relatively low radiopacity, and then adding a thin layer of a highly-radiopaque material, such as gold, to the stent. This approach, which required the use of two separate materials, involved a relatively complicated process in applying the radiopaque material to the stent. Additionally, the use of multiple materials can complicate use and deployment of the stent, particularly where the different materials have different material characteristics, such as different strengths, different biocompatibility, or different responses to temperature changes.

Another approach was to provide a stent with substantially thicker portions at each end. Such an approach provided a stent with highly radiopaque ends, so that a physician could easily view the stent ends during stent delivery.

What has been needed and heretofore unavailable is an improved means of providing a stent with high flexibility, strength, and radiopacity. The present invention satisfies these and other needs.

SUMMARY OF THE INVENTION

The present invention provides a stent with increased bendability and flexibility without comprising the radial strength of the device. The stents of the present invention have sufficient longitudinal flexibility along their longitudinal axis to facilitate delivery through tortuous body lumens, yet remain stable when expanded radially to maintain the patency of a body lumen such as an artery or other vessel, when implanted therein. The present invention in particular relates to unique patterns which permit greater longitudinal flexibility and sufficient radial-expansibility and strength to hold open body lumens. The present invention achieves this enhanced bending through the use of preferential bending points disposed on the stent structure to increase flexibility and bendability when being delivered through the patient's vasculature and later for implantation in the body vessel, particularly in a curved body vessel.

The stents of the present invention can generally include a plurality of adjacent cylindrical elements (often referred to as "rings") which are generally expandable in the radial direction and arranged in alignment along a longitudinal stent axis. The cylindrical elements can be formed in a variety of serpentine wave patterns transverse to the longitudinal axis and contain a plurality of alternating peaks and valleys. At least one interconnecting member extends between adjacent cylindrical elements and connects them to one another. These interconnecting members insure a minimal longitudinal contraction during radial expansion of the stent in the body vessel. The serpentine patterns may have varying degrees of curvature in the regions of peaks and valleys and are adapted so that radial expansion of the cylindrical elements are generally uniform around their circumferences during expansion of the stent from the contracted condition to an implanted condition.

Again, the present invention achieves increased bendability and flexibility of the stent through the use of preferential bending points created on these interconnecting members which connect adjacent cylindrical rings. In this regard, the bending points help the interconnecting members to bend or flex when needed without compromising the radial strength developed by the cylindrical elements. These bending points on the interconnecting members can be created in a number of different ways. For example, the bending point can be achieved by decreasing the width of the strut in order to have a smaller cross-section at one or more points along the length of the interconnecting member. Additionally, the bending point can be created by decreasing the strut thickness at preferential points along the length of the interconnecting member. The present invention can also utilize a combination of decreased strut widths and strut thicknesses to create a highly flexible bending point along the interconnecting members, as well.

In one aspect of the present invention, the preferential bending points can be located at the ends of the interconnecting members which are directly adjacent to the cylindrical elements. Another preferential bending point can be created at about midpoint of the interconnecting member to enable the distance between the cylindrical elements to be reduced as needed, especially when the stent is being implanted in a body vessel having a tight bend radius. As a result, the bending points allow select interconnecting members to bend and shorten as needed in order to conform to the inside radius of a tight curved body vessel. Other interconnecting members of the stent may remain relatively unbent to provide structural stability to the stent.

The number and location of the interconnecting members and the bending points can be varied in order to develop the desired longitudinal flexibility in the stent structure both in the unexpanded, and expanded positions. The use of fewer interconnecting members usually results in a more flexible design since this "frees up" more of the highly flexible peaks of the cylindrical element. Thus, while stent flexibility is derived mainly from the cylindrical rings, the number and location of the interconnecting members can influence the flexibility by constraining or "freeing up" the peaks and valleys. Generally, the greater the longitudinal flexibility of the stent, the easier and the more safely it can be delivered to the implantation site, especially when the implantation site is on a curved section of a body lumen, such as a coronary artery or peripheral blood vessel, and especially in saphenous veins and larger vessels. However, if increased vessel scaffolding is desired, the number of interconnecting members can be increased as needed.

The resulting stent structures are a series of radially expandable cylindrical elements that are spaced longitunally close enough so that small dissections in the wall of a body lumen may be pressed back into position against the lumenal wall, but not so close as to compromise the longitudinal flexibility of the stent both when negotiating through the body lumens in their unexpanded state and when expanded into position. Each of the individual cylindrical elements may rotate slightly relative to their adjacent cylindrical elements without significant deformation, cumulatively providing stents which are flexible along their length and about their longitudinal axis, but which still are very stable in their radial direction in order to resist collapse after expansion.

The stents of the present invention can be readily delivered to the desired target location by mounting it on an expandable member, such as a balloon, of a delivery catheter and passing the catheter-stent assembly lumen to the target area. A variety of means for securing a stent to the extendible member of the catheter for delivery to the desired location are available. It is presently preferred to crimp or compress the stent onto the unexpanded balloon. Other means to secure the stent to the balloon included providing ridges or collars on the inflatable member to restrain lateral movement, using bioabsorbable temporary adhesives, or adding a retractable sheath to cover the stent during delivery through a body lumen. When a stent of the present invention is made from a self-expanding material, such as nickel titanium alloy, a suitable stent delivery assembly which includes a retractable sheath, or other means to hold the stent in its expanded condition prior to deployment, can be utilized.

The serpentine pattern of the individual cylindrical elements can optionally be in phase with each other in order to reduce the contraction of the stent along its length when expanded. The cylindrical elements of the stent are plastically deformed when expanded (except with NiTi alloys or other self-expanding materials) so that the stent will remain the expanded condition and therefore must be sufficiently rigid when expanded when expanded to prevent the collapsed thereof during use. When the stent is formed from superelastic nickel titanium alloys or similar materials, the expansion occurs when the stress of compression is removed. Shape memory alloys, which also include NiTi, can be used as well. Shape memory alloys allow for phase transformation to occur, resulting in the expansion of the stent.

The above and other objects and advantages of this invention will be apparent from the following more detailed description when taken in conjunction with the accompanying drawings of exemplary embodiments.

BRIEF DESCRIPTION OF THE DRAWINGS

FIG. 2 is a side elevational view, in reduced scale, similar to FIG. 1, wherein the stent is expanded within a curved portion of the body vessel where a stenosis is located, pressing outwardly the atherosclerotic plaque and vessel wall to increase the size of the lumen through which blood flows.

FIG. 3 is a side elevational view, partially in section showing the stent of FIG. 2 expanded against the wall of the body vessel after withdrawal of the delivery catheter.

DETAILED DESCRIPTION OF THE PREFERRED EMBODIMENTS

Figure 1:
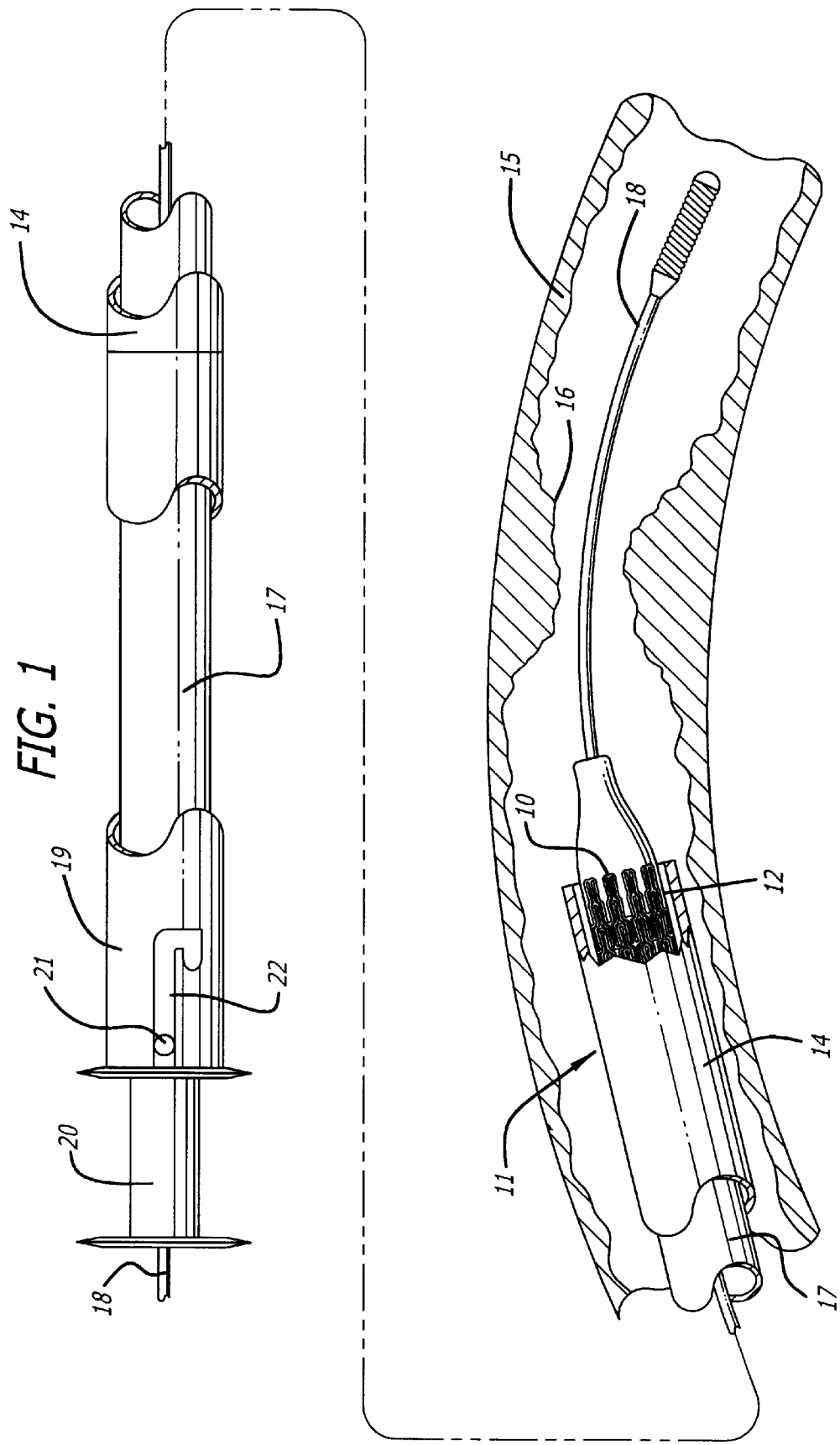
FIG. 1 is a side elevational view, partially in section, of a stent embodying features of the present invention mounted on a delivery catheter and disposed within a damaged body vessel.

Referring now to the drawings, in which reference numerals represent like or corresponding elements across the drawings, and particularly FIGS. 1–3 thereof, there is generally shown a stent 10 made in accordance with the present invention which is mounted onto a delivery catheter 11. The stent 10 is a high precision patterned tubular device, which in the embodiment shown in FIG. 1 is a self-expanding stent which is used to open and maintain open a portion of a body vessel, such as an artery, and prevent restenosis from occurring in the area of treatment. The stent 10 typically comprises a plurality of radially expanded cylindrical elements or rings 12 disposed generally coaxially and connected by interconnecting members 13 disposed therebetween adjacent cylindrical elements 12. The delivery catheter 11 includes a restraining sheath 14 which extends over the contracted stent 10 until the stent 10 is ready for deployment within an artery 15, or other blood vessel or body vessel of a patient. The artery 15, as shown in FIGS. 1–3, has a stenosis 16 which has occluded a portion of the arterial passageway.

Each radially expandable cylindrical element 12 of the stent 10 may be independently expanded. Therefore, the shape of the stent can be other than cylindrical, e.g. tapered, to facilitate implantation of the stent 10 in a variety of body lumen shapes.

Figure 9:
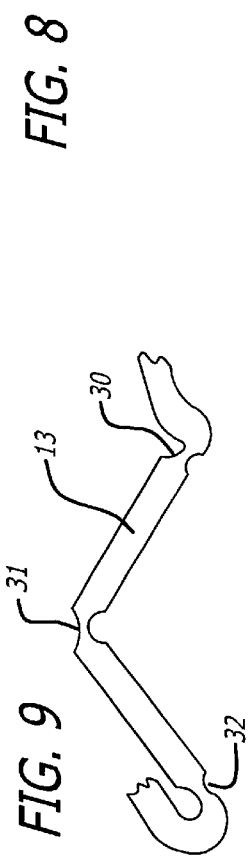
FIG. 9 is an exploded side elevational view of an interconnecting member shown in FIG. 8.
Figure 8:
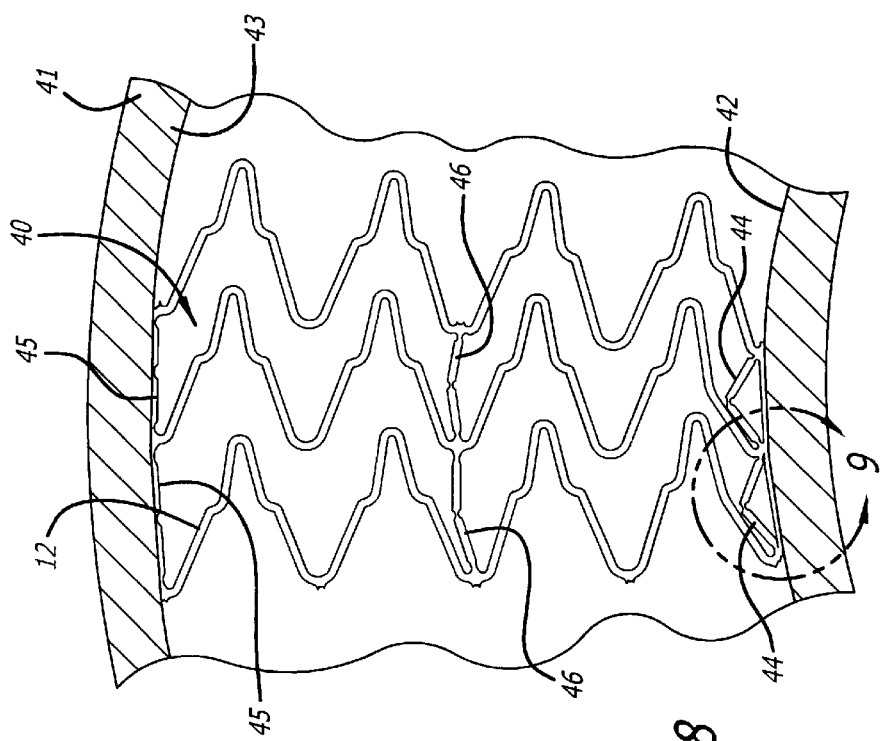
FIG. 8 is a side elevational view of a portion of a stent implanted in a body vessel having a curved radius which shows the bending of certain interconnecting members of the stent that allows the stent to conform to the curvature of the body vessel.

As is shown in FIGS. 1–3, the artery 15 has a curved portion to it where the stenosis 16 has developed. Reference should be made to FIGS. 8 and 9 and the description herein which show in expanded detail the ability of a stent made in accordance with the present invention to conform to the curvature of the patient's vasculature. Moreover, while the stent 10 is shown implanted at a curved location in the patient's vasculature, it should be appreciated that the present invention could still be implanted in a straight section of a body vessel which requires treatment. In such a situation, while there may not be a need for the stent to bend when implanted to conform with the patient's anatomy, the present invention will still provide flexibility to the stent as it is being delivered through the often tortuous passage ways of the patient's vasculature.

The delivery of the stent 10 can be accomplished in the following manner. The stern 10 is first mounted onto a mounting region formed on an inner catheter member 17 at the distal extremity of the delivery catheter 11 with the restraining sheath 14 being placed over the contracted stern 10. The catheter/stent assembly is introduced within the patient's vasculature in a conventional Seldinger technique through a guiding catheter (not shown). A guide wire 18 is disposed across the stenosed arterial section and then the catheter-stern assembly is advanced over a guide wire 18 until the stent is directly under the slenosis 16. The restraining sheath 14 is then retracted, allowing the slent to expand to a larger diameter to press up against the atherosclerotic plaque which has built up on the vessel wall, as illustrated in FIG. 2. While not shown in the drawing, the artery is preferably expanded slightly by the expansion of the stein to seal or otherwise fix the stent to prevent movement. In some circumstances during the treatment of stenotic portions of an artery, the artery may have to be expanded considerably in order to facilitate passage of blood or other fluid therethrough. The retraction of the restraining sheath 14 isaccoinplished at the. proximal end of the delivery catheter 11 by virtue of a proximal handle portion which can he manipulated by the physician outside of the patient. As is shown in FIG. 1. the restraining sheath 14 has a proximal handle 19 which extends coaxially over the proximal handle portion 20 of the inner catheter member 17. The distal end of the restraining sheath 14 which covers the stent 10 can be simply retracted by the physician by pulling back on the proximal handle 19 a certain distance which assures that the distal most end of the sheath has been retracted from the stent 10. A raised projection 21 located on the handle 20 of the inner catheter member 17 moves within a slot 22 formed on the proximal handle 19. The length of this slot assures that the precise amount of retraction is achieved. It should be appreciated that the inner catheter member 17 may include an abutting shoulder, which can be formed by a proximal band marker, to create a raised shoulder against which the proximal end of the stent 10 contacts as the restraining sheath 14 is retracted. The raised shoulder should prevent the stent 10 from moving hack proximally with the sheath as it is being retracted by the physician.

The particular embodiment of the stant 10 shown in FIGS. 1–5 is directed to a self-expanding stent which can be made from a self-expanding material, such as NiTi, or similar material. However, a stent made in accordance with the present invention could be either self-expanding or balloon expandable, depending upon the type of material utilized to manufacture the stent. It should also be appreciated that although the stent 10 is shown being utilized to treat an area in which atherosclerotic plaque has built up against the wall of the artery, it could also be used to hold up a detached lining, or other abnormality, of a patient. Moreover, a stent made in accordance with the present invention could be utilized in any one of a number of different body vessels, including but not limited to carotid arteries, coronary arteries and renal arteries. The stent could be used for primary stenting purposes, i.e., to directly enlarge the opening in the artery or it could be utilized in conjunction with predilatation in which plaque is initially expanded in the area of treatment by a balloon dilatation catheter. Thereafter, the stent could be placed in the predilatated area of treatment.

Figure 4:
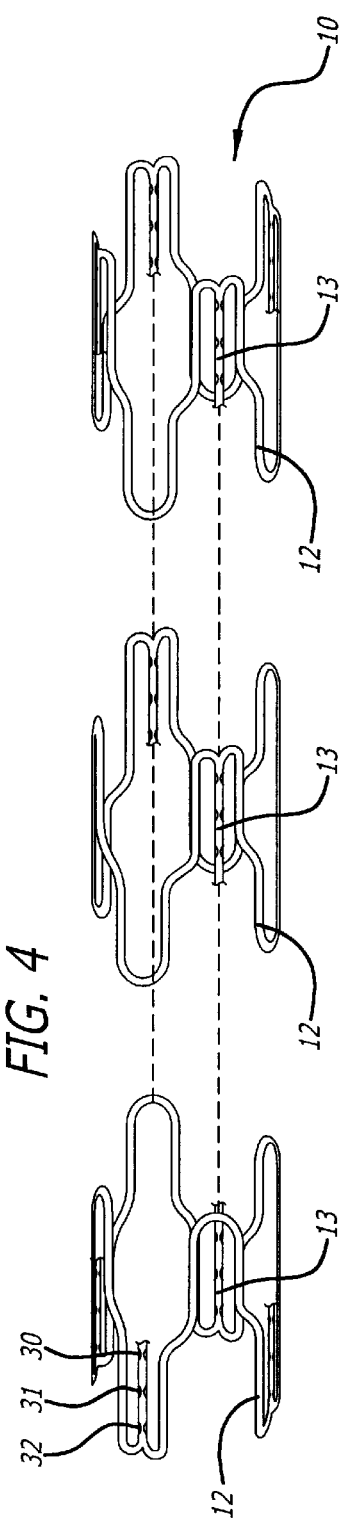
FIG. 4 is an exploded perspective view, partially broken, of the stent shown in FIG. 1 in its expanded implanted state.

FIG. 4 is an enlarged perspective view of the stent 10 of FIG. 1 which illustrates in greater detail just one example of a stent structure which can be made in accordance with the present invention. Each interconnecting element 13 on one side of a cylindrical element 12 is placed to achieve maximum flexibility for a stent. In the embodiment shown in FIG. 4, the stent has three interconnecting elements 13 between adjacent radially expandable cylindrical elements 12 which are 120 degrees apart. Each interconnecting element 13 on one side of a cylindrical element 12 can be directly aligned with interconnecting members located on the other side of the cylindrical element to form three continuous spines that extend longitudinally along the length of the stent. This alignment of the interconnecting elements 15 results in a stent which is longitudinally flexible and helps prevent the stent from foreshortening when expanded to the implanted diameter. It should be appreciated that various configurations for the placement of interconnecting elements are still possible. For example, the interconnecting elements 13 could also be offset radially 60 degrees from interconnecting members located on the other side of a cylindrical element, as well. Also, the number of interconnecting members can also be varied. While the disclosed embodiment shows interconnecting members which form more continuous longitudinal spines along the length of the stent, it should be appreciated that one, two or more continuous spines could be created without departing from the spirit and scope of the present invention. Moreover, the location of the interconnecting members can be varied in any different stent configurations that can be made in accordance with the present invention. All of the interconnecting elements of an individual stent could be secured to either the peaks or valleys of the undulating structural elements in order to prevent shortening of the stent during expansion thereof. The number of undulations may also be varied to accommodate placement of interconnecting elements 13, e.g. at the peaks of the undulations or along the sides of the undulations as shown in FIG. 5.

Figure 5:
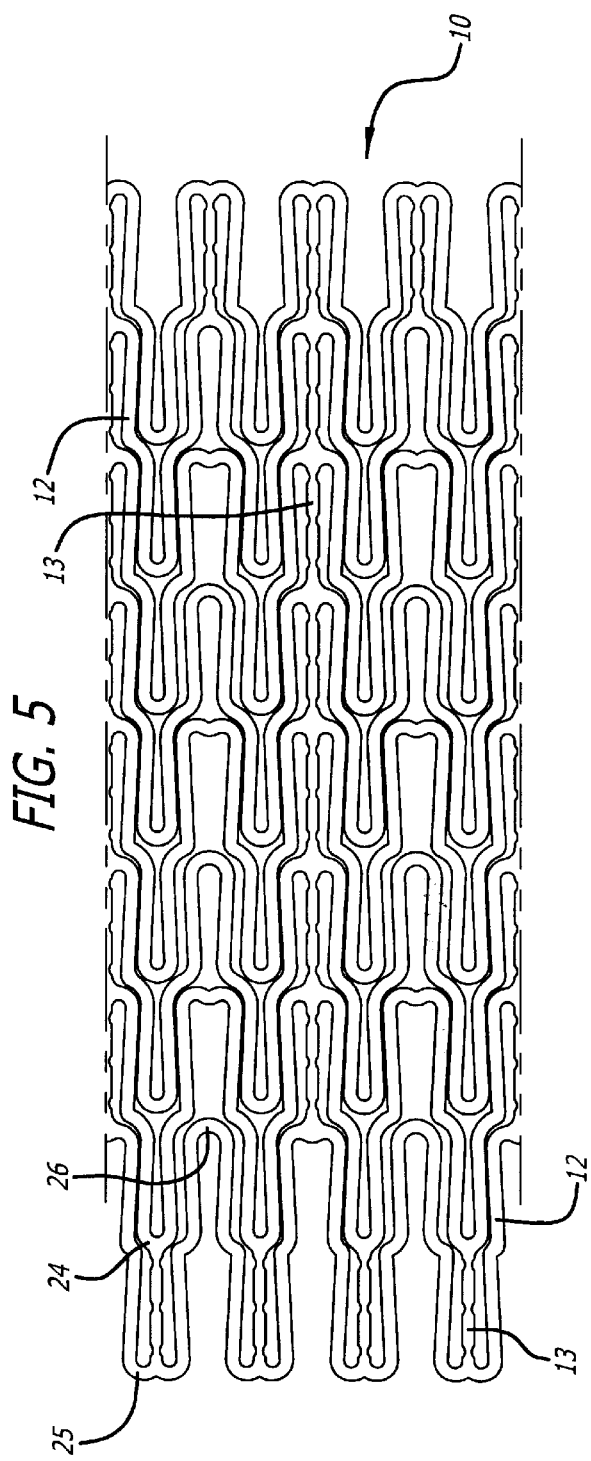
FIG. 5 is a plan view, in enlarged scale, of a flattened section of a stent shown in FIG. 4.

As best observed in FIGS. 4 and 5, cylindrical elements 12 are in the form of a serpentine pattern. As previously mentioned, each cylindrical element 12 is connected by interconnecting elements 13. Serpentine pattern is made up of a plurality of U-shaped members 24, W-shaped members 25, and inverted U-shaped members 26, each having a different radius so that expansion forces are more evenly distributed over the various members.

Figure 6:
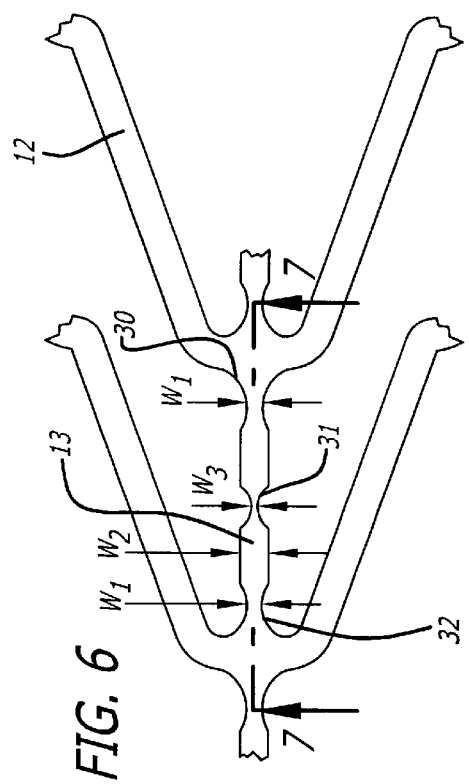
FIG. 6 is a side elevational view showing the bending points formed on one interconnecting member of a stent embodying features of the present invention.

Referring now to FIGS. 6–9, which shows the bending points 30 which are formed on the interconnecting members 13 used in conjunction with the present invention, one or more of the individual interconnecting members which connect adjacent cylindrical elements 12 can have one or more bending points 30 formed therein. As is shown in FIG. 6, the interconnecting member 13 is shown with three bending points 30, 31 and 32 located along the length of the interconnecting member. This is but one example of the location and number of bending points which can be used in accordance with the present invention. Again, referring specifically to the embodiment shown in FIG. 6, there are two bending points 30 and 32 which are located near the ends of the interconnecting member where attachment is made to each of the adjacent cylindrical elements 12. These particular bending points 30 and 32 are shown as having a small cross-sectional strut width $W_1$ than the strut width $W_2$ forming the majority of the interconnecting member 13. The bending point 31 has a strut width $W_3$ which is even smaller than the strut width $W_2$ associated with the other two other bending points 30 and 32. This particular bending point 31 is located substantially near the center of the interconnecting member 13 so as to provide a bending point which allows the strut to fully bend, as is shown in FIGS. 8 and 9, in order to conform with a curved section of vessel wall. It should be appreciated that the strut widths $W_1$ and $W_3$ can be varied as needed to create the necessary bending action desired. In this regard, any number of bending points could be placed on the interconnecting member, along with different strut widths to achieve the type of bending desired.

Figure 7:
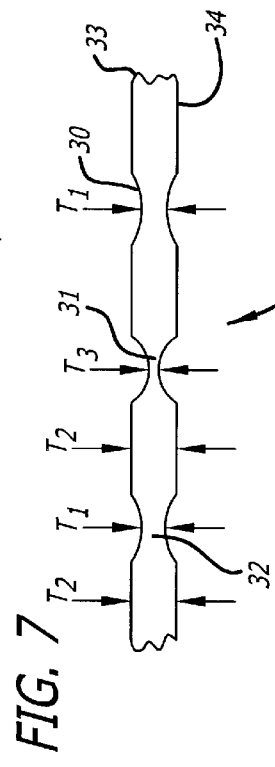
FIG. 7 is a cross-sectional view taken along line 7—7 of the varying strut thickness which forms the bending points on the interconnecting member of FIG. 6.

Referring now to FIG. 7, the bending points 30–32 are shown in cross-sectional view as having varying strut thicknesses which also create the necessary bending action. As is seen in FIG. 7, the strut which forms the interconnecting member 13 has different wall thicknesses at the location of the various bending points 30–32. Each of the struts which forms the interconnecting members or cylindrical elements of the stent has both an outside surface 33 and an inside surface 34 which defines the wall thickness of the stent. As can be seen in FIG. 7, the strut wall thickness $T_1$ at the bending points 30 and 32 are essentially the same while the area directly adjacent to these bending points has a wall thickness $T_2$, which can be greater than $T_1$. In a like manner, bending point 32 has a wall thickness $T_3$ which is smaller than the strut wall thickness $T_2$ which extends along the length of the interconnecting member. Again, this decrease in the wall thickness enhances the stent's ability to flex and bend as needed to negotiate the often tortuous anatomy of the patient and to conform with the anatomy once implanted at the treatment site. Again, the number of bending points, along with the wall thickness associated with each bending point, can be varied as needed to achieve the necessary bendability of the stent. The number and location of bending points in FIGS. 6 and 7 are shown by way of example only, and are by no means intended to limit the scope of the present invention.

Referring now to FIG. 8, a representation of a stent 40 is shown which includes a number of interconnecting members 13 used to connect adjacent cylindrical elements 12 together. The stent 40 is placed in a body vessel having curvature to better illustrate the function of the present invention. As can be seen in FIG. 8, the body vessel 41 includes a vessel wall 42 having an inside radius which is less than the outside radius associated with the opposite side of the wall 43. As a result, the stent 40 has to bend considerably at the interconnecting members located in close proximity to the inside wall 42 in order to conform with the patient's vasculature. As can be seen in this particular drawing, the interconnecting members 44 are substantially bent at the bending points 30–32 in order to reduce the distance between adjacent rings as needed to accommodate the size and shape of the body vessel 40. The remaining interconnecting members 45 located near the outer wall 42 are shown substantially straight since little or no bending would be needed in order to properly maintain the cylindrical elements in proper alignment with each other. Other intermediate interconnecting members 46 located between the members 44 and 45 those depicted in FIG. 8 which would bend slightly to accommodate the curvature of the body vessel 40. While this representation of the bending achieved by the interconnecting members as shown in FIG. 8 is somewhat dramatic for illustrative purposes only, it nevertheless shows the effect that the various bending points will provide to the stent in order to increase bending and conformability to the patient's anatomy.

It should be appreciated that the present invention can be used to make stents which do not incorporate cylindrical rings as described herein, but rather, other structural elements, such as zig zag patterns, coil patterns, and the like to create a composite stenting device.

In FIG. 5, the stent is depicted flat for ease of illustration. The embodiments depicted herein can be formed as cylindrically-shaped stents that are generally manufactured from tubing by laser cutting as described below.

The stents of the present invention can be made in many ways. One suitable method of making the stent is to cut a thin-walled tubular member, such as stainless steel tubing or nickel-titanium, to remove portions of the tubing in the desired pattern for the stent, leaving relatively untouched the portions of the metallic tubing which are to form the stent. It is preferred to cut the tubing in the desired pattern by means of a machine-controlled laser.

The tubing may be made of suitable biocompatible material such as stainless steel. The stainless steel tube may be alloy-type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | .025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

A suitable composition of Nitinol used in the manufacture of the stent of the present invention is approximately 55% nickel and 45% titanium (by weight) with trace amounts of other elements making up about 0.5% of the composition. The austenice finish transformation temperature is between about 0° C. and 20° C. in order to achieve superelasticity. The austenite finish temperature is measured by the bend and free recovery tangent method. The upper plateau strength is about a minimum of 60,000 psi with an ultimate tensile strength of a minimum of about 155,000 psi. The permanent set (after applying 8% strain and unloading), is less than approximately 0.5%. The breaking elongation is a minimum of 10%. It should be appreciated that other compositions of Nitinol can be utilized, as can other self-expanding alloys, to obtain the same features of a self-expanding stent made in accordance with the present invention.

The stent of the present invention can be laser cut from a tube of super-elastic (sometimes called pseudo-elastic) nickel titanium (Nitinol) as well. The stent diameters can cut with the same stent pattern, and the stent is expanded and heat treated to be stable at the desired final diameter. The stent can be electro polished to obtain a smooth finish with a thin layer of titanium oxide placed on the surface. The stent is usually implanted into the target vessel which is smaller than the stent diameter so that the stent applies a force to the vessel wall to keep it open.

The stent tubing may be made of suitable biocompatible material besides super-elastic nickel-titanium (NiTi) alloys. In this case the stent would be formed full size but deformed (e.g. compressed) into the restraining sheath of the delivery catheter to facilitate intraluminal delivery to a desired intraluminal site. Upon release of the restraining sheath when the stent reaches the desired intraluminal location, the stent expands due to the self-expanding properties of the material.

The stent diameters are very small, so the tubing from which it is made must necessarily also have a small diameter. For PTCA applications, typically the stent has an outer diameter on the order of about 1.65 mm (0.065 inches) in the unexpanded condition, the same outer diameter of the hypotube from which it is made, and can be expanded to an outer diameter of 5.08 mm (0.2 inches) or more. The wall thickness of the tubing is about 0.076 mm (0.003 inches). For stents implanted in other body lumens, such as PTA applications, the dimensions of the tubing are correspondingly larger. This stent is also designed for carotid applications, so the outer diameter of the tubing would typically be about 0.095 inches with a wall thickness of about 0.007 inches. The diameters of a carotid stent typically would be about 5–10 mm. While it is beneficial to laser cut tubing to create the stent, those skilled in the art will realize that the stent can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent. Further details on how the tubing can be cut by a laser are found in U.S. Pat. Nos. 5,759,192 (Saunders) and 5,780,807 (Saunders), which have been assigned to Advanced Cardiovascular Systems, Inc.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

The individual bending points to be formed in the interconnecting members can be cut when the stent pattern is being cut into the tubular member. In this regard, since the bending points on the interconnecting members are somewhat small, a fine laser may be required in order to fine cut the tubing. The smaller wall thickness at the bending points can be achieved by utilizing the same machine-controlled laser used to create the stent pattern. For example, the laser could ablate a particular amount of material from the outer surface of the tubular member to create a reduced strut thickness at the bending points. In this regard, the laser would selectively remove portions of the outer surface at the location where the bending point will be created. In this regard, the desired wall thickness can be achieved at particular bending points. Likewise, wall thicknesses at other bending points can be achieved utilizing the machine-controlled laser.

Alternatively, the tubing could be pre-set with a wall thickness having a nominal thickness in the areas where the majority of the struts are to be formed with less-than-nominal thicknesses in the areas where the bending points are to be located. Thereafter, the laser can cut the tubing precisely at the point where the reduced or less-nominal-thickness occurs in order to create the bending point. In this regard, a properly encoded computer-controlled laser can achieve the desired bending points for the particular pattern which is being used to form the stents. It should be appreciated that some experimentation may be required in order to determine the optimal points where the bending points should be placed on a given interconnecting member. Also, it may not be necessary to place bending points on all of the interconnecting members, just those which will be necessary to develop the bending characteristics which are desired. In this regard, the stent can be modeled on a computer program which could be used to determine the precise positions where the bending points should be placed on a particular stent pattern.

The elements or struts can also be formed by etching techniques disclosed and claimed in U.S. Pat. No. 5,421,955 issued to Lilip Lau, William M. Hartigan and John J. Frantzen on Jun. 6, 1995, for "Expandable Stents and Method For Making Same." The elements or struts may also be formed as by etching techniques disclosed and claimed in U.S. Pat. No. 5,514,154 issued on May 7, 1996, to Lilip Lau, William M. Hartigan and John J. Frantzen for "Expandable Stents And Method For Making Same."

The stents of the present invention can be used in any vascular application where the vessel requires support to remain open and allow blood to flow through the vessel. The stents may also be used for biliary stenting. The delivery of the stents may follow any conventional procedure. Although the embodiments have been illustrated and described in terms of the use of an intravascular stent, it will be apparent to persons of ordinary skill in the art that the stents of the present invention can be used in other instances in the body, such as, but not limited to, the urethra and esophagus and to expand prostatic urethras in cases of prostate hyperposia.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed:

1. A stent for implanting in a body lumen, comprising:
a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent; and
a plurality of interconnecting members extending between cylindrical elements to connect adjacent cylindrical elements, some of the interconnecting members having one or more bending points formed therein for promoting the bendabilty of the interconnecting member, wherein each interconnecting member is formed of a strut having a substantially uniform strut wall thickness and each bending point is formed by reducing the strut wall thickness at the location of the bending point.

2. The stent of claim 1, wherein:
each bending point is a weakened area of the strut forming the interconnecting member.

3. A stent for implanting in a body lumen, comprising:
a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent; and
a plurality of interconnecting members extending between cylindrical elements to connect adjacent cylindrical elements, some of the interconnecting members having one or more bending points formed therein for promoting the bendabilty of the interconnecting member, wherein:
each interconnecting member is formed of a strut having a substantially uniform strut width and each bending point is formed by reducing the strut width at the location of the bending point.

4. A stent for implanting in a body lumen, comprising:
a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stert; and
a plurality of interconnecting members extending between cylindrical elements to connect adjacent cylindrical elements, some of the interconnecting members having one or more bending points formed therein for promoting the bendabilty of the interconnecting member, wherein:
  each interconnecting member is formed of a strut having a substantially uniform strut wall thickness and strut width and each bending point is formed by reducing the strut wail thickness and strut width at the location of the bending point.

5. A stent for implanting in a body lumen, comprising:
a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent; and
a plurality of interconnecting members extending between cylindrical elements to connect adjacent cylindrical elements, some of the interconnecting members having one or more bending points formed therein for promoting the bendabilty of the interconnecting member, wherein:
  each interconnecting member has at least one bending point formed therein.

6. A stent for implanting in a body lumen, comprising:
a plurality of adjacent cylindrical elements each having a circumference extending around a longitudinal stent axis and being substantially independently expandable in a radial direction, each cylindrical element being formed in a generally serpentine wave pattern transverse to the longitudinal axis of the stent; and
a plurality of interconnecting members extending between cylindrical elements to connect adjacent cylindrical elements, some of the interconnecting members having one or more bending points formed therein for promoting the bendabilty of the interconnecting member, wherein:
  some interconnecting members have three bending points formed therein.

7. The stent of claim 6, wherein:
two of the three bending points are formed at the area where the interconnecting member is connected to a cylindrical element.

8. The stent of claim 7, wherein:
the third bending point is located substantially near the center of the interconnecting member.

9. The stent of claim 1, wherein:
the stent is formed from a biocompatible material selected from the group consisting of stainless steel, tungsten, tantalum, titanium alloys, and thermal plastic polymers.

10. A stent for implanting in a body lumen, comprising:
a plurality of adjacent cylindrical elements each formed from a strut having a strut wall thickness and a strut wall width and being substantially independently expandable in a radial direction; and
a plurality of interconnecting members each formed from a strut having a strut wall thickness and a strut wall width and extending between adjacent cylindrical elements to connect adjacent cylindrical elements together, some of the interconnecting members having a plurality of bending points formed therein for promoting the bendability of the interconnecting member, wherein:
  each interconnecting member has a strut width narrower than the strut width of the cylindrical elements.

11. The stent of claim 10, wherein:
the bending point is formed by reducing the strut wall thickness on the interconnecting member.

12. The stent of claim 10, wherein:
the stent is formed from a biocompatible material selected from the group consisting of stainless steel, tungsten, tantalum, nickel titanium alloys, and thermal plastic polymers.

13. A stent for implanting in a body lumen, comprising:
a plurality of adjacent cylindrical elements each formed from a strut having a strut wall thickness and a strut wall width and being substantially independently expandable in a radial direction; and
a plurality of interconnecting members each formed from a strut having a strut wall thickness and a strut wall width and extending between adjacent cylindrical elements to connect adjacent cylindrical elements together, some of the interconnecting members having a plurality of bending points formed therein for promoting the bendability of the interconnecting member, wherein:
  each bending point is formed by weakening the strut forming the interconnecting member to allow the bending points to bend before the remainder of the strut bends once subjected to an external force.

14. A stent for implanting in a body lumen, comprising:
a plurality of adjacent cylindrical elements each formed from a strut having a strut wall thickness and a strut wall width and being substantially independently expandable in a radial direction; and
a plurality of interconnecting members each formed from a strut having a strut wall thickness and a strut wall width and extending between adjacent cylindrical elements to connect adjacent cylindrical elements together, some of the interconnecting members having a plurality of bending points formed therein for promoting the bendability of the interconnectng member, wherein:
  the bending point is formed on a strut by reducing the strut width of the interconnecting member.

15. A stent for implanting in a body lumen, comprising:
a plurality of adjacent cylindrical elements each formed from a strut having a strut wall thickness and a strut wall width and being substantially independently expandable in a radial direction; and
a plurality of interconnecting members each formed from a strut having a strut wall thickness and a strut wall width and extending between adjacent cylindrical elements to connect adjacent cylindrical elements together, some of the interconnecting members having a plurality of bending points formed therein for promoting the bendability of the interconnecting member, wherein:
  the bending point is formed by reducing both the strut wall thickness and strut width of the interconnecting member.

16. A stent for implanting in a body lumen, comprising:
a plurality of adjacent cylindrical elements each formed from a strut having a strut wall thickness and a strut wall width and being substantially independently expandable in a radial direction; and
a plurality of interconnecting members each formed from a strut having a strut wall thickness and a strut wall width and extending between adjacent cylindrical elements to connect adjacent cylindrical elements together, some of the interconnecting members having a plurality of bending points formed therein for promoting the bendability of the interconnecting member, wherein:

each interconnecting member has a plurality of bending points formed therein.

17. The stent of claim 16, wherein:

each interconnecting member has three bending points formed therein.

18. The stent of claim 17, wherein:

two of the three bending points are formed at the area where the interconnecting member is connected to a cylindrical element.

19. The stent of claim 18, wherein:

the third bending point is located substantially near the center of the interconnecting member.

* * * * *